United States Patent [19]

Ponpipom et al.

[11] 4,259,324

[45] Mar. 31, 1981

[54] IMMUNOLOGIC ADJUVANT THIO GLYCOSIDE COMPOUNDS AND COMPOSITIONS

[75] Inventors: Mitree M. Ponpipom, Branchburg; Tsung-Ying Shen, Westfield; Robert L. Bugianesi, Colonia, all of N.J.

[73] Assignee: Merck & Co., Inc., Rahway, N.J.

[21] Appl. No.: 62,586

[22] Filed: Jul. 31, 1979

[51] Int. Cl.$^3$ .................... A61K 31/70; A61K 31/705; C07H 5/10
[52] U.S. Cl. .................................. 424/180; 424/182; 536/4; 536/5; 536/121
[58] Field of Search .................... 424/180, 182; 536/4, 536/121, 5

[56] References Cited

U.S. PATENT DOCUMENTS 4,189,471  2/1980  Ponpipom et al. .................. 424/182

OTHER PUBLICATIONS

Behling et al., "Jour. of Immunology", vol. 117, No. 3, Sep. 1976, pp. 847–851.

Primary Examiner—Johnnie R. Brown
Attorney, Agent, or Firm—Donald J. Perrella; Julian S. Levitt

[57] ABSTRACT

Compounds of the formulae Y—R wherein Y is 1-thio-$\beta$-L-fucose, 1-thio-$\beta$-D-galactose or 1-thio-$\beta$-lactose and R is 2-(1-adamantyl)ethyl, 3-[(p-tetrafluorophenethyl)phenyl]propyl, 6-(5-cholesten-3$\beta$-yloxy)hex-3-ynl, oleyl, or hexadecyl are useful immunologic adjuvants in vaccines.

8 Claims, No Drawings

IMMUNOLOGIC ADJUVANT THIO GLYCOSIDE COMPOUNDS AND COMPOSITIONS

BACKGROUND OF THE INVENTION

The present invention relates to an immunologic adjuvant and, more particularly, to novel glycolipid immunologic adjuvant and to improved vaccine formulations containing a novel glycolipid immunologic adjuvant.

Broadly considered, the vaccines utilized at the present time are "fluid vaccines". The term "fluid vaccine" designates a suspension of an immunogenic or desensitizing agent in water or in a medium comprising a single, aqueous, liquid phase. The principal purpose for employment of an immunologic adjuvant is to achieve a more durable immunity of a higher level employing a smaller antigenic mass in a fewer number of doses than could be achieved by administration of the equivalent aqueous antigen. It may be noted that development of an immunologically satisfactory and pharmacologically acceptable adjuvant is a prime essential for the preparation of workable multivalent killed virus vaccines which are effective and practical in the prevention of viral, bacterial, mycoplasmal or rickettsial diseases.

OBJECTS OF THE INVENTION

It is an object of the present invention to provide new glycolipid compounds. Another object is to provide methods for preparing these glycolipid compounds. A further object is to provide vaccine compositions containing these glycolipid compounds. These and other objects of the present invention will be apparent from the following description.

SUMMARY OF THE INVENTION

Compounds of the formulae Y-R wherein Y is 1-thio-$\beta$-L-fucose, 1-thio-$\beta$-D-galactose or 1-thio-$\beta$-lactose and R is 2-(1-adamantyl)ethyl, 3-[(p-tetrafluorophenethyl)phenyl]propyl, 6-(5-cholesten-3$\beta$-yloxy)hex-3-ynl, oleyl, or hexadecyl are useful immunologic adjuvants in vaccines.

DETAILED DESCRIPTION

The compounds of the present invention which are useful as immunologic adjuvants are the following:
1. 2-(1-adamantyl)ethyl 1-thio-$\beta$-L-fucopyranoside.
2. 2-(1-adamantyl)ethyl 1-thio-$\beta$-D-galactopyranoside.
3. 2-(1-adamantyl)ethyl 1-thio-$\beta$-lactoside.
4. 3-[(p-tetrafluorophenethyl)phenyl]propyl 1-thio-$\beta$-L-fucopyranoside.
5. 3-[(p-tetrafluorophenethyl)phenyl]propyl 1-thio-$\beta$-D-galactopyranoside.
6. 3-[(p-tetrafluorophenethyl)phenyl]propyl 1-thio-$\beta$-lactoside.
7. 6-(5-cholesten-3$\beta$-yloxy)hex-3-ynl 1-thio-$\beta$-L-fucopyranoside.
8. 6-(5-cholesten-3$\beta$-yloxy)hex-3-ynl 1-thio-$\beta$-D-galactopyranoside.
9. 6-(5-cholesten-3$\beta$-yloxy)hex-3-ynl 1-thio-$\beta$-lactoside.
10. Oleyl 1-thio-$\beta$-L-fucopyranoside.
11. Oleyl 1-thio-$\beta$-D-galactopyranoside.
12. Oleyl 1-thio-$\beta$-lactoside.
13. Hexadecyl 1-thio-$\beta$-L-fucoyranoside.
14. Hexadecyl 1-thio-$\beta$-L-galactopyranoside.
15. Hexadecyl 1-thio-$\beta$-lactoside.

The novel adjuvants of the invention may be employed to potentiate the antibody response of antigenic materials. The term "antigen" and "antigenic material" which are used interchangeably herein include one or more non-viable immunogenic or desensitizing (antiallergic) agents of bacterial, viral or other origin. The antigen component of the products of the invention may consist of a dried powder, an aqueous solution, an aqueous suspension and the like, including mixtures of the same, containing a non-viable immunogenic or desensitizing agent or agents.

The aqueous phase may conveniently be comprised of the antigenic material in a parenterally acceptable liquid. For example, the aqueous phase may be in the form of a vaccine in which the antigen is dissolved in a balanced salt solution, physiological saline solution, phosphate buffered saline solution, tissue culture fluids or other media in which the organism may have been grown. The aqueous phase also may contain preservatives and/or substances conventionally incorporated in vaccine preparations. The adjuvant emulsions of the invention may be prepared employing techniques well known to the art.

The antigen may be in the form of purified or partially purified antigen derived from bacteria, viruses, rickettsia or their products, or extracts of bacteria, viruses, or rickettsia, or the antigen may be an allergen such as pollens, dusts, danders, or extracts of the same or the antigen may be in the form of a poison or a venom derived from poisonous insects or reptiles. In all cases the antigens will be in the form in which their toxic or virulent properties have been reduced or destroyed and which when introduced into a suitable host will either induce active immunity by the production therein of antibodies against the specific microorganisms, extract or products of microorganisms used in the preparation of the antigen, or, in the case of allergens, they will aid in alleviating the symptoms of the allergy due to the specific allergen. The antigens can be used either singly or in combination; for example, multiple bacterial antigens, multiple viral antigens, multiple mycoplasmal antigens, multiple rickettsial antigens, multiple bacterial or viral toxoids, multiple allergens or combinations of any of the foregoing products can be combined in the aqueous phase of the adjuvant composition of this invention. Antigens of particular importance are derived from bacteria such as *B. pertussis, Leptospira pomona* and *icterohaemorrhagiae, S. typhosa, S. paratyphi A* and *B, C. diphtheriae, C. tetani, C. botulinum, C. perfringens, C. feseri* and other gas gangrene bacteria, *B. anthracis, P, pestis, P. multocida, V. cholerae, Neisseria meningitidis, N, gonorrheae, Hemophilus influenzae, Treponema pollidum,* and the like; from viruses as polio virus (multiple types), adeno virus (multiple types), parainfluenza virus (multiple types), measles, mumps. respiratory syncytial virus, influenza (various types), shipping fever virus (SF4), Western and Eastern equine *encephalomyelitis,* Japanese *B. encephalomyelitis,* Russian Spring Summer *encephalomyelitis,* hog cholera virus, Newcastle disease virus, fowl pox, rabies, feline and canine distemper and the like viruses, from rickettsiae and epidemic and endemic typhus or other members of the spotted fever group, from various spider and snake venoms or any of the known allergens for example from ragweed, house dust, pollen extracts, grass pollens and the like.

The compounds of the present invention are prepared by reacting a per-O-acetyl-1-thio-glycopyranose, wherein the glycopyanose is L-fucose, D-galactose or lactose, with a halide of the formula R-X wherein R is 2-(1-adamantyl)ethyl, 3-[(-p-tetrafluorophenethyl)phenyl]propyl, 6-(5-cholesten-3β-yloxy)hex-3-nyl, oleyl or hexadecyl and X is halogen, preferably iodo or bromo. The reactants are generally employed in equimolar amounts. The reaction is generally carried out in an aprotic solvent in which the reactants are soluble. Some suitable solvents are, for example, acetonitrile, benzene and halgenated solvents such as dichloromethane, carbon tetrachloride and chloroform. The reaction is carried out in the presence of equimolar amounts of an aid aceptor such as a tertiary amine, e.g., triethylamine, 1,5-diazabicyclo[5,4,0]undec-5-ene (DBU) or 1,5-diazabicyclo[4,3,0]non-5-ene (DBN). When the acid acceptor is a tertiary amine such as triethylamine, the reaction is generally conducted under nitrogen at about room temperature for from about 1 to about 3 days. When the acid acceptor is a tertiary amine such as DBU or DBN, the reaction is usually complete within about 0.5 to about 3 hours at about room temperature.

The reaction mixture is partitioned between dichloromethane and water. The organic layer is dried and concentrated to a syrup which is put on a column of silica gel and eluted with appropriate solvents. The desired fractions are combined and evaporated to give the R-substituted per-O-acetyl-1-thioglycopyranoside which is deblocked by suitable means, e.g., treatment with an anionic ion exchange resin such as Bio-Rad AG 1-X2 in ethanol-tetrahydrofuran or by saponification in the presence of a base such as sodium methoxide in methanol, to give the final product.

The following examples illustrate the present invention without, however, limiting the same thereto. All temperatures are expressed in degrees Celsius.

EXAMPLE 1

2-(1-Adamantyl)ethyl 1-thio-β-L-fucopyranoside

A solution of 2-(1-adamantyl)ethyl p-toluene-sulfonate (4.0 g) and sodium iodide (2.5 g) in 2-butanone (20 ml) is heated for 2 hours under reflux. The cooled solution is filtered and concentrated to a residue which is partitioned between dichloromethane and water. The organic layer is washed with aqueous sodium thiosulfate and water. The dried solution is evaporated to a crystalline mass which is recrystallized from ethanol to give 2-(1-adamantyl)ethyl iodide (2.0 g), m.p. 93°–94°. An analytical sample is obtained by recrystallization from the same solvent, m.p. 97°–98°.

A solution of 2,3,4-tri-O-acetyl-1-thio-β-L-fucopyranose (2.14 g, 7 mmol) and 2-(1-adamantyl)ethyl iodide (2.03 g, 7 mmol) in dichloromethane (40 ml) containing triethylamine (0.71 g) is kept under nitrogen for 3 days. The reaction mixture is washed successively with N hydrochloric acid, aqueous sodium bicarbonate and water. The dried solution is concentrated to a residue which is taken up in ethanol to remove crystals (0.3 g, 2-(1-adamantyl)ethyl iodide). The mother liquor is put on a silica gel column and eluted with 1% methanol in chloroform. The desired fractions are pooled and evaporated to give 2-(1-adamantyl)ethyl 2,3,4-tri-O-acetyl-1-thio-β-L-fucopyranoside (1.8 g, 66%), $[\alpha]_D + 18°$ (c, 1.5, chloroform). Deblocking of this material with sodium methoxide in methanol affords the title compound, m.p. 130°–131°, $[\alpha]_D + 31°$ (c, 1.07, chloroform).

EXAMPLE 2

3-[(p-Tetrafluorophenethyl)phenyl]propyl 1-thio-β-L-fucopyranoside

A solution of 1-phenyl-p-bromophenyltetrafluoroethane (10 g, 30 mmol) in benzene (15 ml) is added dropwise over 15 minutes to a solution of n-butyllithium (16 ml, 36 mmol) (2.17 molar in hexane) in benzene (15 ml). This is followed by the addition of trimethylene oxide (2.0 g, 35 mmol) in benzene (6 ml). The reaction mixture is heated for 4 hours under reflux. The cooled solution is washed with water, dried, and concentrated to dryness. Crystallization from petroleum ether-anhydrous ether gives 3-[(p-tetrafluorophenethyl)phenyl]propanol (3.6 g), m.p. 47°–49°.

A solution of 3-[(p-tetrafluorophenethyl)phenyl]propyl p-toluenesulfonate (650 mg, obtained from 3-[p-tetrafluorophenethyl)phenyl]propanol via p-toluenesulfonylation) and sodium iodide (600 mg) in 2-butanone (20 ml) is heated for 2 hours under reflux. The mixture is filtered and concentrated to a residue which is partitioned between dichloromethane and water. The organic layer is washed with sodium thiosulfate and water. The dried solution is evaporated to a crystalline mass (550 mg), m.p. 66°–68°. Recrystallization from ethanol affords 3-[p-tetrafluorophenethyl)phenyl]propyl iodide, m.p. 73°–75°.

A solution of 2,3,4-tri-O-acetyl-1-thio-β-L-fucopyranose (1.65 g, 4 mmol) and 3-[(p-tetrafluorophenethyl)phenyl]propyl iodide (1.25 g, 4 mmol) in dichloromethane (25 ml) containing triethylamine (0.56 g) is stored under nitrogen overnight. The reaction is worked up in the normal manner to give 3-[(p-tetrafluorophenethyl)phenyl]propyl 2,3,4-tri-O-acetyl-1-thio-β-L-fucopyranoside (1.5 g, 64%), m.p. 138°–139.5°. Deblocking of this material in the usual way affords 3-[(p-tetrafluorophenethyl)phenyl]propyl 1-thio-β-L-fucopyranoside, m.p. 63°–65° (aqueous ethanol), $[\alpha]_D + 22°$ (c, 0.96, chloroform).

EXAMPLE 3

6-(5-Cholesten-3β-yloxy)hex-3-ynl 1-thio-β-L-fucopyranoside

A solution of 2-(5-cholesten-3β-yloxy)ethyl chloride (17 g, 38 mmol) and sodium iodide (8.5 g, 57 mmol) in 2-butanone (200 ml) is heated for 5 hours under reflux. The mixture is concentrated to a residue which is partitioned between chloroform and water. The organic layer is washed with sodium thiosulfate, water, dried and evaporated to dryness. Crystallization from ether-methanol affords 2-(5-cholesten-3β-yloxy)ethyl iodide (15.8 g, 77%), m.p. 86°–88°.

Triphenylmethyl chloride (122 g, 0.44 mol) is added to a solution of but-3-yne-1-ol (25 g, 0.36 mol) in dichloromethane (400 ml) containing pyridine (50 ml) and stirred overnight at room temperature. The reaction mixture is filtered and washed with cold dilute hydrochloric acid, aqueous sodium bicarbonate and water. The dried solution is concentrated to a solid which is crystallized from ether-petroleum ether to give 4-triphenylmethyloxybut-1-yne (60 g), m.p. 97°–99° (ether-petroleum ether).

A solution of phenyllithium (16.8 ml. 0.03 mol) (1.8 M in ether-benzene) is added dropwise under nitrogen to a solution of 4-triphenylmethyloxybut-1-yne (9.36 g, 0.03 mol) in freshly distilled dry tetrahydrofuran (200 ml) kept at −78°. The solution is then warmed to 0° and a solution of 3-(5-cholesten-3β-yloxy)ethyl iodide (16.2 g, 0.03 mol) in dry tetrahydrofuran (100 ml) is added, and the reaction mixture is heated for 8 hours under reflux. The solution is concentrated to a residue which is taken up in ether and washed twice with water, dried, and evaporated to dryness. Crystallization from isopropanol gives 6-(5-cholesten-3β-yloxy)-1-(triphenylmethyloxy)-hex-3-yne (21 g, 97%), m.p. 112°–113°.

A suspension of 6-(5-cholesten-3β-yloxy)-1-(triphenylmethyloxy)hex-3-yne (21 g) in p-dioxan (40 ml) is heated on a steam cone until dissolution. This is followed by the addition of 90% acetic acid (30 ml) until turbidity, and the reaction mixture is heated overnight at 100°. Water (15 ml) is added and the mixture is concentrated to a small volume. Ether and petroleum ether are added and crystals (triphenylmethanol) are filtered and discarded. The filtrate is concentrated to dryness and put on a silica gel column and eluted with 20% ether in petroleum ether. The desired compound, 6-(5-cholesten-3β-yloxy)hex-3-yne-1-ol, is isolated as an oil (7.0 g).

p-Toluenesulfonyl chloride (2.1 g, 11 mmol) is added to a solution of 6-(5-cholesten-3β-yloxy)hex-3-yne-1-ol (3.57 g, 7.4 mmol) in pyridine (25 ml) at 0°. The solution is stored overnight at 5° and poured into ice water. The product is extracted with chloroform and washed with dilute hydrochloric acid, aqueous sodium bicarbonate and water. The dried solution is evaporated to a syrup (3.3 g) which is dissolved in 2-butanone (50 ml). Sodium iodide (1 g) is added and the mixture is heated for 4 hours under reflux. The solution is concentrated to a residue which is partitioned between chloroform and water. The organic layer is washed with 5% sodium thiosulfate and water, dried, and evaporated to a crystalline mass. Recrystallization from isopropanol gives 6-(5-cholesten-3β-yloxy)hex-3-yne-1-iodide (2.6 g), m.p. 82°–83°.

A solution of 2,3,4-tri-O-acetyl-1-thio-β-L-fucopyranose (500 mg, 1.6 mmol) and 6-(5-cholesten-3β-yloxy)hex-3-yne-1-iodide (940 mg, 1.6 mmol) in dichloromethane (30 ml) containing triethylamine (162 mg) is kept under nitrogen for 2 days at room temperature. The solution is washed with dilute hydrochloric acid, aqueous sodium bicarbonate and water. The dried solution is concentrated to a residue which is put on a silica gel column and eluted with 30% ether in petroleum ether. The desired fractions are pooled and evaporated to give 6-(5-cholesten-3β-yloxy)hex-3-ynl 2,3,4-tri-O-acetyl-β-L-fucopyranoside (900 mg, 73%), $[\alpha]_D + 3.4°$ (c, 1.5, chloroform).

Deblocking of this material with sodium methoxide in methanol gives 6-(5-cholesten-3β-yloxy)-hex-3-ynl 1-thio-β-L-fucopyranoside (65%), m.p. 137°–138° (methanol), $[\alpha]_D - 6.5°$ (c, 1.5, chloroform).

EXAMPLE 4

Oleyl 1-thio-β-L-fucopyranoside

A solution of 2,3,4-tri-O-acetyl-1-thio-β-L-fucopyranose (2.0 g, 6.5 mmol) and oleyl iodide (2.5 g, 6.6 mmol) in dichloromethane (40 ml) containing triethylamine (1 ml) is kept under nitrogen for 2 days at room temperature. The solution is worked up in the normal manner and the resulting syrup is column chromatographed on silica gel with 2–10% ethyl acetate in chloroform as eluents. Oleyl 2,3,4-tri-O-acetyl-1-thio-β-L-fucopyranoside is isolated as a syrup (1.2 g, 32%), $[\alpha]_D + 26°$ (c, 2.19, chloroform).

A sample of this material is deblocked with sodium methoxide in methanol to give oleyl 1-thio-β-L-fucopyranoside (67%), $[\alpha]_D + 30°$ (c, 2.24, chloroform).

EXAMPLE 5

Hexadecyl 1-thio-β-L-fucopyranoside

A solution of 2,3,4-tri-O-acetyl-1-thio-β-L-fucopyranose (2.0 g, 6.5 mmol) and 1-bromohexadecane (2.0 g, 6.5 mmol) in dichloromethane (40 ml) containing triethylamine (1 ml) is kept under nitrogen for 2 days at room temperature. The reaction is worked up in the usual manner to give a syrup which is put on a silica gel column and eluted with 2–5% ethyl acetate in chloroform. The desired fractions are pooled and concentrated to dryness. Crystallization from aqueous ethanol gives hexadecyl 2,3,4-tri-O-acetyl-1-thio-β-L-fucopyranoside (1.9 g, 55%), m.p. 49°–50°, $[\alpha]_D + 9°$ (c, 1.5, chloroform).

Deblocking of this material with sodium methoxide in methanol gives the title compound in 91% yield, m.p. 96.5°–97.5° (methanol), $[\alpha]_D + 10°$ (c, 0.74, chloroform).

EXAMPLE 6

An aqueous suspension of the final product of Example 1 is sterile filtered and added in levels of 0.005 mg and 0.05 mg to 2 samples of bivalent whole influenza vaccine (A Victoria and B Hong Kong strains). Similar adjuvant vaccine preparations are prepared using the final products of examples 2, 3, 4 and 5.

EXAMPLE 7

The procedure of Example 6 is repeated using subunit A Victoris influenza vaccine.

What is claimed is:

1. A compound of the formula

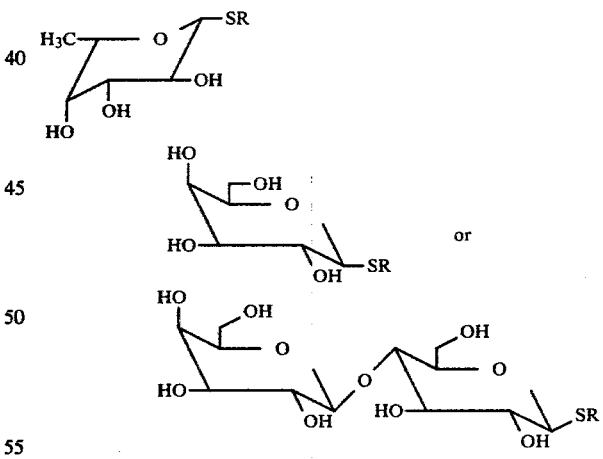

wherein R is

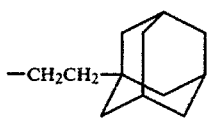

,

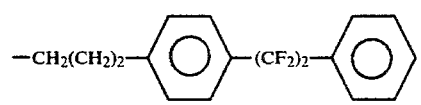

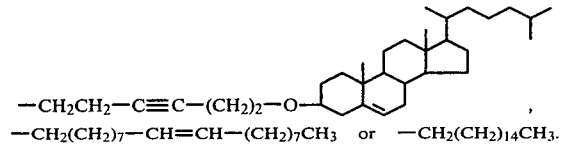

—CH₂(CH₂)₇—CH=CH—(CH₂)₇CH₃ or
—CH₂(CH₂)₁₄CH₃.

2. A compound of claim 1 wherein Y is 1-thio-β-L-fucose.

3. A compound of claim 1 wherein Y is 1-thio-β-D-galactose.

4. A compound of claim 1 wherein Y is 1-thio-β-lactose.

5. A compound of claim 1 having the name
2-(1-adamantyl)ethyl 1-thio-β-L-fucopyranoside,
2-(1-adamantyl)ethyl 1-thio-β-D-galactopyranoside,
2-(1-adamantyl)ethyl 1-thio-β-lactoside,
3-[(p-tetrafluorophenethyl)phenyl]propyl 1-thio-β-L-fucopyranoside,
3-[(p-tetrafluorophenethyl)phenyl]propyl 1-thio-β-D-galactopyranoside,
3-[(p-tetrafluorophenethyl)phenyl]propyl 1-thio-β-lactoside,
6-(5-cholesten-3β-yloxy)hex-3-ynl 1-thio-β-L-fucopyranoside,
6-(5-cholesten-3β-yloxy)hex-3-ynl 1-thio-β-D-galactopyranoside,
6-(5-cholesten-3β-yloxy)hex-3-ynl 1-thio-β-lactoside,
Oleyl 1-thio-β-L-fucopyranoside,
Oleyl 1-thio-β-D-galactopyranoside,
Oleyl 1-thio-β-lactoside,
Hexadecyl 1-thio-β-L-fucopyranoside,
Hexadecyl 1-thio-β-L-galactopyranoside,
Hexadecyl 1-thio-β-lactoside.

6. A per-O-acetylated compound of claim 1.

7. An immunologic adjuvant composition comprising an antigenic material and a compound of claim 1 in an amount effective to exert an adjuvant effect.

8. An immunologic adjuvant composition comprising a compound of claim 1 in an amount effective to exert an adjuvant effect and a pharmaceutically acceptable carrier.

* * * * *